United States Patent [19]

Ferguson

[11] Patent Number: 5,092,179

[45] Date of Patent: Mar. 3, 1992

[54] DYNAMIC MATERIAL TESTING SYSTEM HAVING INDEPENDENT CONTROL OVER SPECIMEN DEFORMATION AND STRAIN RATE AND A METHOD FOR USE THEREIN

[75] Inventor: Hugo S. Ferguson, Averill Park, N.Y.

[73] Assignee: Duffers Scientific, Inc., Poestenkill, N.Y.

[21] Appl. No.: 672,690

[22] Filed: Mar. 8, 1991

[51] Int. Cl.⁵ .............................................. G01D 7/02
[52] U.S. Cl. ..................................................... 73/790
[58] Field of Search ................. 73/790, 794, 795, 818, 73/825; 374/51

[56] References Cited

U.S. PATENT DOCUMENTS

| | | |
|---|---|---|
| 2,754,675 | 7/1956 | More . |
| 2,904,994 | 9/1959 | Claxton . |
| 3,057,190 | 10/1962 | Minke . |
| 3,397,572 | 8/1968 | Stolz et al. . |
| 3,404,562 | 10/1968 | MacGlashan, Jr. et al. . |
| 3,457,779 | 7/1969 | Hahn et al. . |
| 3,473,371 | 10/1969 | Loeb . |
| 3,818,751 | 6/1974 | Karper et al. . |
| 3,916,679 | 11/1975 | Voll et al. . |
| 4,074,569 | 2/1978 | Sambrook et al. . |
| 4,109,516 | 8/1978 | Fuxa . |
| 4,523,475 | 6/1985 | Bills, Jr. et al. . |
| 4,674,318 | 6/1987 | Bourdon . |
| 4,687,343 | 8/1987 | Raffalski . |

*Primary Examiner*—Robert Raevis
*Attorney, Agent, or Firm*—Peter L. Michaelson

[57] ABSTRACT

Apparatus, and an accompanying method for use therein, for a dynamic material testing system, and particularly for one that tests a specimen by compressively deforming its work zone and that has independent control over specimen deformation (strain) and strain rate. The apparatus can also simultaneously direct resistance heat or conductively cool the specimen, under controlled conditions, in order to establish isothermal planes at a desired substantially uniform temperature throughout the specimen work zone before, during and after each compressive deformation thereof.

26 Claims, 5 Drawing Sheets

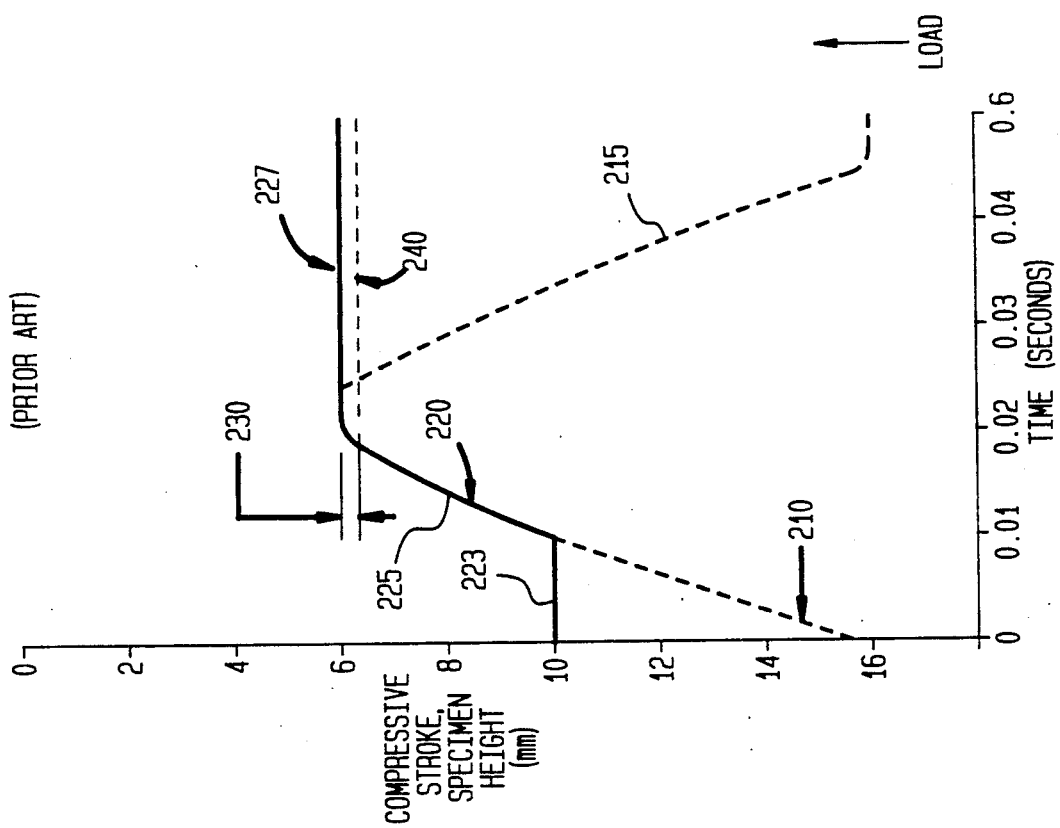
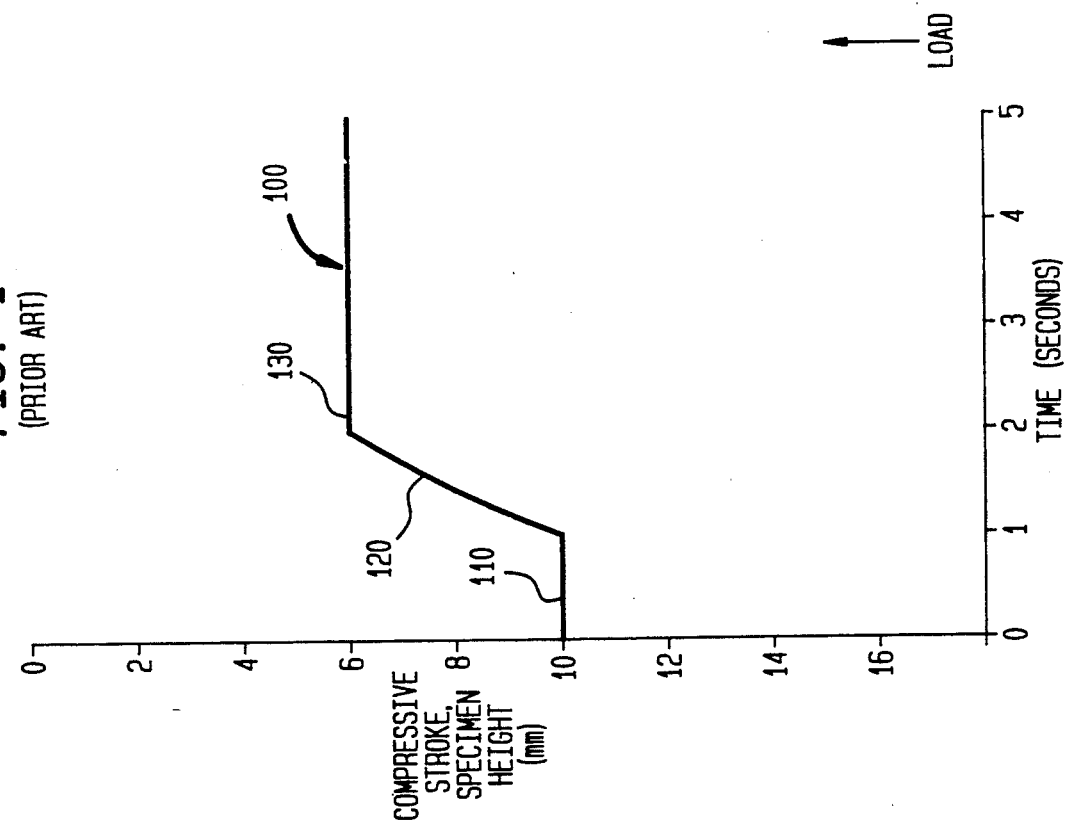

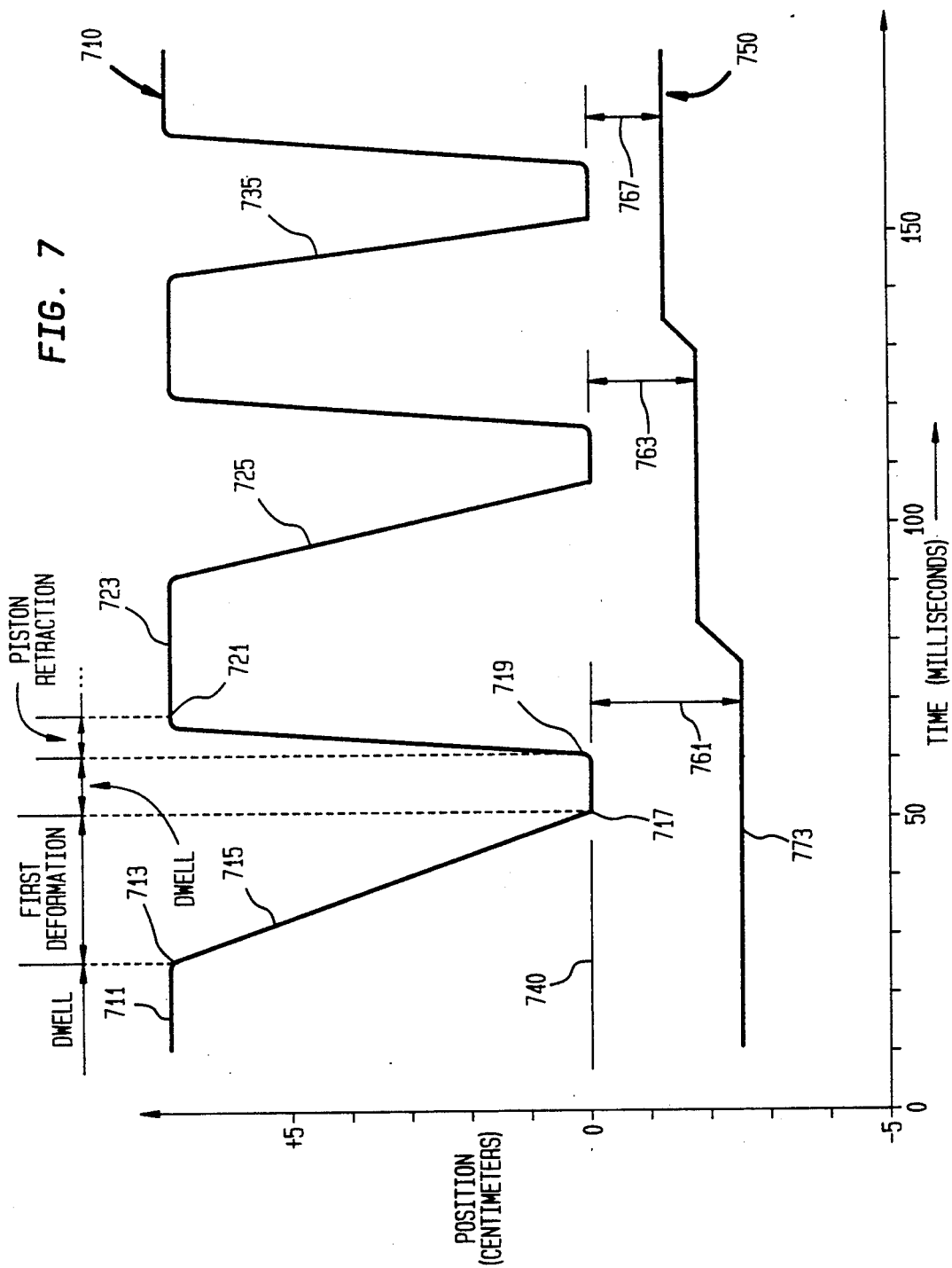

DYNAMIC MATERIAL TESTING SYSTEM HAVING INDEPENDENT CONTROL OVER SPECIMEN DEFORMATION AND STRAIN RATE AND A METHOD FOR USE THEREIN

BACKGROUND OF THE DISCLOSURE

1. Field of the Invention

The invention relates to apparatus, and an accompanying method for use therein, for a dynamic material testing system that has independent control over specimen deformation and strain rate. In addition to controllably deforming a work zone of a specimen, the system can also simultaneously direct resistance heat or conductively cool the specimen, under controlled conditions, in order to establish isothermal planes at a desired substantially uniform temperature throughout the work zone.

2. Description of the Prior Art

Metallic materials play an indispensable role as an essential component of an enormous number of different products. Currently, these materials are typically fabricated through rolling, forging or extruding operations into sheet, strip or wire, i.e. intermediate products, which are thereafter appropriately formed into a shape of a final product. Unfortunately, the financial costs associated with establishing a production mill to produce an intermediate product are staggering.

Nevertheless, an increasing number of new rolling mills has come on-line within the last few years. As a result, mill operators are experiencing very intense marketplace competition for finished rolled stock which, in turn, necessitates that mills be run to produce rolled material of constantly improving quality at ever decreasing cost. Not unexpectedly, this competition is becoming increasingly more intense as additional production facilities come on-line. Accordingly, in view of this competition and the enormous cost associated with establishing and operating a rolling mill, profit margins on rolled stock tend to be rather slim. As such, marketplace economics now dictate that a mill must be established and operated with as little margin of error as possible. Consequently, to reduce various financial risks to manageable levels, a substantial need has arisen to accurately simulate rolling operations in, typically, a laboratory environment and learn their effects on material characteristics before implementing these operations on an operating production mill. The simple reason for this is that once a mill is in production, any subsequent down-time tends to be extremely costly and thus is best avoided. Inasmuch as accurate simulations permit mill parameters to be optimized off-line, then, by substantially eliminating mill down-time, such simulations advantageously permit higher production yields while significantly reducing research costs. Fortunately, simulations are substantially less capital intensive, typically by at least several orders of magnitude, and significantly less time-consuming than establishing a so-called small pilot mill or, where possible, even a small sample mill in order to obtain the desired metallurgical results. Furthermore, since rolling mill simulations can yield extensive data from specimens that are considerably smaller than normal production sized materials, appreciable material savings and hence significant cost economies result if a production mill were to be accurately simulated rather than being taken off-line (out of service) to provide test materials. Accordingly, a substantial and growing need exists in the art for apparatus that can physically simulate a rolling mill with a high degree of accuracy.

Ideally, a proper rolling mill simulation should permit a speciment to undergo the same mechanical deformation and thermal processing that will be encountered in a desired rolling mill. While an accurate simulation is relatively easy to perform for a rolling mill having a single stand, accurate simulations become increasingly difficult to accomplish for multi-stand mills. Specifically, with modern rolling mills, strip stock is often passed through a multi-stand mill at a relatively high velocity. These mills quickly deform the material using several deformations in series and obtained through successive roll stands within a relatively short time, often on the order of a few milliseconds, between successive deformations. In addition, the temperature of the strip also tends to change from each stand to the next.

Several techniques exist in the art for simulating a rolling mill. One well-known technique, as described in, for example, U.S. Pat. Nos. 4,109,516 (issued to J. Fuxa on Aug. 29, 1978) and 3,457,779 (issued to E. Hahn et al on July 29, 1969), involves use of the so-called cam plastometer. Here, a specimen is fixedly held. A ram controllably and rapidly strikes the specimen with a given stroke distance to deform the specimen in an amount equal to that which would be encountered in a mill stand. The motion of the ram is governed by a cam follower that rotates against a cam, with the latter being rotated by an hydraulic motor and a flywheel. Each rotation of the cam moves the ram to compress the specimen once. The size and shape (profile) of the cam, particularly that of its lobe, is set to obtain desired amounts of true strain and true strain rate in the deformed specimen. Unfortunately, this technique possesses several drawbacks which limit its utility. First, cam plastometers are unable to simulate modern multi-stand mills. In this regard, older cam plastometers have generally been limited to imparting a single amount of deformation to a specimen and thus could only simulate a single rolling mill stand. Recently, cam plastometers have been developed that are capable of imparting two successive deformations to a specimen thereby possessing a capability to simulate two stand mills. However, modern rolling mills frequently possess more than two stands and frequently four or more. Cam plastometers have not yet been developed that can simulate that many mill stands. Furthermore, while a cam plastometer can accurately reproduce a strain profile for a rolling operation, a cam must be replaced by one having a significantly different cam profile if a widely differing strain profile is to be generated by that plastometer. The operations inherent in machining a new cam with an appropriate profile and then substituting one cam for another each time a different strain profile is desired are both time consuming and inconvenient. Consequently, cam plastometers, due to their limited simulation ability and attendant difficulties of use, are presently being employed less and less for mill simulation.

A second well-known technique for simulating a rolling mill generally involves using a computer-controlled material testing system in which a specimen is grasped in a fixed mount and then controllably struck by a ram mounted, via a rod, to an end of an servo-controlled hydraulic piston. The rate of travel of the ram determines the strain rate of the specimen with the distance through which the ram compresses the specimen determining its deformation. Unfortunately, this technique generally suffers from excessive dwell time, poor end-of-stroke control and deviations from a programmed true strain rate during deformation, all of which adversely limit the ability of this technique to accurately simulate modern medium to high speed multi-stand rolling mills.

Specifically, to simulate each stand of a multi-stand rolling mill with this second technique, the computer situated within the material testing system would be appropriately programmed by an operator to provide a controlled series of "hits" to the specimen, with each hit causing a desired strain rate and compressive deformation in the specimen. Once a simulation commenced, the computer would first set the speed and stroke distance of the ram to provide the desired strain rate and deformation for the first hit on the specimen, then control the hydraulic system to retract the ram into its starting position and thereafter appropriately operate a hydraulic servo-value that controls the piston to permit the ram to strike the specimen with the proper velocity for this hit and then continue compressing the specimen for a desired distance, with this process repeating for each successive hit.

Mechanical reality, as dictated by the laws of physics, is such that as the speed of the ram increases, higher forces are needed to stop and reverse its direction. In a modern medium to high speed multi-stand rolling mill, the typical material transit time between the last and next-to-last roll stands therein is on the order of tens of milliseconds and sometimes as small as only a few milliseconds. Furthermore, rapid deformation of the type encountered in a rolling mill necessitates that the ram travel at a high rate of speed when impacting the specimen for each hit. Accordingly, if the performance of such a mill is to be accurately simulated, then the dwell time between the next-to-last and last deformations that are imparted to a specimen should match this transit time. Unfortunately, to provide such a short dwell time, unmanageably large forces would likely be required to: (a) stop the ram at the end of the next-to-last hit, (b) then reverse its motion to fully retract it into its starting position, and (c) finally strike the specimen at high speed to cause the desired strain rate in the specimen for the last hit—all within a comparable time interval. Furthermore, apart from the necessary forces, hydraulic servo-values and associated hydraulic components often do not provide a sufficiently fast response to accommodate the required movement of the ram. This, in turn, also tends to increase the minimum dwell time of the system and thereby reduce the maximum rate at which the specimen can be successively hit.

Furthermore, control of the position and velocity of the ram at the end of its stroke tends to be quite imprecise. Specifically, during simulation of multi-stand mills, the height of the specimen incrementally decreases as it is successively hit. Inasmuch as true strain, $\epsilon$, for compressive deformation is defined by: $\epsilon = -\ln(h_0/h)$, where h is the final specimen height and $h_0$ is the initial height, the true strain rate, $(d\epsilon/dt)$, is given by: $(1/h)(dh/dt)$. Thus, if the final thickness of the specimen is relatively small, then the true strain rate obtained during the final hit may be correspondingly high. For example, if a ram moving at a controlled stroke rate of 1000 mm/second hits the specimen to yield a final compressive deformation that reduces the specimen to 2 mm in height, then the initial true strain rate at impact in the specimen, i.e. the "entrance" true strain rate, is 500/second.

Relatively low strain rates, e.g. 2/second, such as that typically encountered in rolling plate in a single stand mill, and corresponding final deformations in a test specimen can be readily obtained using conventional servo-hydraulically actuated rams. However, relatively high strain rates, such as illustratively 100–500/second or even less as would typically be encountered in the final stand in a medium to high speed rolling mill, are very difficult to accurately obtain in a test specimen using such a ram. At such high strain rates, the ram must travel and accelerate over a given distance in order to impact the specimen at a velocity that will produce a correct entrance true strain rate in the specimen. However, in practice, the ram generally overshoots and does not stop at the exact position at which a desired amount of deformation is produced in the specimen. For small deformations, the ram velocity can not be maintained without significant over-travel of the ram. This over-travel produces unwanted additional strain in the specimen. As the strain rate increases and the specimen deformation accordingly decreases for successive hits, the additional strain caused by over-travel becomes relatively large compared to the initial specimen height prior to a hit. Since the final stand(s) of a modern multi-stand rolling mill typically imparts a relatively small deformation but a relatively large true strain rate to rolled strip, the strain in the specimen, including that produced by over-travel of the servo-hydraulically actuated ram, by a conventional material testing system significantly deviates from the strain which would be produced by each of these stands in the mill thereby corrupting the simulated results. If the over-travel is relatively significant as compared to the desired specimen height, then the additional strain imparted to the specimen becomes intolerably high. Concomitantly, if the desired deformation is achieved at the instant the ram stops moving, then the ram velocity and hence the resulting true strain rate are both generally too low, particularly near the end of its movement, to accurately simulate actual mill conditions in the specimen.

As to programmed true strain rate, if a conventional servo-hydraulically actuated ram produces a correct programmed entrance true strain rate, then the precision with which the servo in the material testing system will maintain this rate throughout the ensuing deformation will typically be based on a ratio between the time during which the speimen is deformed, i.e. the deformation time, and the response time of the system. As either the response time shortens or deformation time increases, then increasingly precise true strain rate control can result. Hence, the ram would be increasingly able to produce a desired true strain rate at any position along its stroke during the deformation. However, since response time is often comparable to a fast deformation time, a servo-hydraulically actuated ram is generally incapable of accurately changing the true strain rate it imparts to a specimen during a fast deformation. For that reason, relatively precise control of the true strain rate produced during a fast deformation can only be accomplished if the material testing system is operated such that the ram moves at a correct velocity upon impacting the specimen and does not stop as soon as the desired strain is attained but rather continues to move thereafter. Unfortunately, this causes over-shoot. As discussed above, the additional strain caused by ram over-shoot, particularly at high true strain rates and small deformations, can produce gross inaccuracies in simulating actual conditions associated with the final stand(s) of a medium to high speed multi-stand rolling mill.

Consequently as the speed of modern multi-stand rolling mills increases, the inability of conventional material testing systems that employ servo-hydraulically actuated rams to provide the requisite high speed control over strain rate and deformation causes these systems to become increasingly less suitable for simulating these mills.

In an attempt to alleviate these limitations, it is known in the art to place an adjustable height mechanical stop between a moving platen to which the ram is mounted and a fixed platen to which the specimen is secured. This stop may comprise one or two wedges. The base of each wedge abuts against the fixed platen with its inclined surface facing the moving platen and particularly a complementary shaped surface thereon. The wedge(s) is connected to a servo-hydraulic cylinder and can be extended or retracted thereby in a direction transverse to ram displacement to provide a stop of a desired thickness between the two platens. In operation, the wedge(s) is first positioned such that the ram produces a desired amount of deformation in the specimen. Thereafter, the moving platen is accelerated towards the fixed platen with movement of the former being halted upon contact with the wedge(s). The area of each wedge is much larger than that of the cross-section of the specimen so that a relatively small amount of elastic strain is produced in each wedge when it is struck by the moving platen. While this arrangement advantageously eliminates over-travel of the ram and its attendant adverse consequences, it disadvantageously requires that, for a constant true strain rate, the ram be decelerated during each hit and that the ram stop at a new position at the end of each successive hit. This, in turn, greatly complicates the programming of such a system in order to achieve a true mill process simulation. Specifically, when programs for use in such a material testing system are written to control the movement of the ram, the program must cause the ram to decelerate while the specimen is being deformed if the true strain rate is to be either held constant or controlled in accordance with the performance of the mill. Since the ram is traveling at a high velocity at the beginning of the hit and the total amount of deformation during a hit may be very small (the ram travel may illustratively be a fraction of a millimeter for some "final" hits), then, owing to response limitations of the system, properly slowing (decelerating) the ram to produce a constant true strain rate (or other programmed rate) in the specimen may be quite difficult to achieve in practice. Furthermore, the changing stop position of the ram for each successive hit further complicates programming the needed ram deceleration and hence significantly increases the difficulty associated with programming a true mull process simulation.

Thus, a need still exists in the art for a material testing system, and specifically for apparatus for inclusion therein, that can accurately hit a specimen under test to produce a desired amount of deformation therein at a relatively high true strain rate but without generating substantially any over-travel. In addition, this apparatus should permit a desired relatively high entrance true strain rate to be produced in the specimen and then maintained throughout the ensuing deformation. Both the true strain rate and the deformation should be independently adjustable. Furthermore, the apparatus should be capable of successively generating such hits with reduced dwell time. Such a system would advantageously find use in accurately simulating modern high speed multi-stand rolling mills.

SUMMARY OF THE INVENTION

My invention advantageously overcomes the deficiencies associated with material testing systems known in the art that utilize both a servo-hydraulically actuated ram to compress a specimen and wedge stop(s) situated between moving and fixed platens.

Advantageously, my inventive apparatus permits specimen deformation (thickness reduction) and strain rate to be independently and precisely controlled and programmed for each and every successive deformation, and from deformation to deformation, regardless of the number of such deformations that is being used.

In accordance with my invention, a first actuator, preferably a servo-controlled hydraulic actuator that is mounted to a fixed frame, produces a force along a first pre-defined direction. First and second deforming means, which are illustratively separate corresponding first and second electrically conductive anvils, abuttingly engage with opposing sides of a specimen. Force transferring and stopping means are situated in abutting engagement with the first anvil and move the first anvil, in response to the force, along the first pre-defined direction in order to compressively deform the specimen and thereafter terminate any further movement of the first anvil as soon as that the specimen has been compressed by a pre-determined amount. In addition, moving means, which is also mounted to the fixed frame, is used to move the specimen, and the first and second deforming means by the pre-determined amount and in a second direction opposite to the first pre-defined direction prior to commencement of the compressive deformation. The moving means is illustratively actuated by a second servo-controlled hydraulic cylinder coupled to the fixed frame and the second anvil. Inasmuch as the moving means exhibits a very high degree of stiffness while the specimen is being compressed, the moving means as well as the specimen advantageously experience substantially no movement in the first pre-defined direction while the specimen is being compressively deformed.

The strain rate and final strain induced in the specimen during the compressive deformation are respectively and substantially independently determined by velocity of the force transferring and stopping means along the first direction, specifically the velocity of the piston rod ("compressive piston") emanating from the first hydraulic cylinder, during the deformation and a distance that the moving means is moved in the second pre-defined direction prior to the commencement of the deformation.

Specifically, in accordance with a preferred embodiment of my invention, each of the two anvils is movable with respect to the other. The portion of the specimen that is situated between both anvils and hence will undergo compressive deformation is referred to herein as the "work zone". Both anvils and the specimen are encircled by a stop assembly, illustratively containing a substantially U-shaped cross stop and twin stop bars extending therefrom to a first cross head, which, in turn, is secured to the frame. The first anvil is moved by a first shaft that extends through a second cross head which is also secured to the frame. This shaft is pushed by the compression piston, with the stroke of the shaft being limited by a stop plate, which is also part of the stop assembly, whenever that plate abuttingly engages against the cross stop. The second anvil is connected to one end of a second shaft which extends through the first cross head. The second shaft can be precisely positioned to incrementally move the specimen by a predefined distance towards the compression piston and, by doing so, displace the stop plate from the cross stop by just that distance in order to control the exact amount of strain that will be imparted to the specimen by each successive hit. The velocity of the compression piston governs the velocity of the first anvil and hence the strain rate induced in the specimen during its compressive deformation.

Permitting the second anvil to be positionable independently of the stroke distance of the compression piston advantageously allows the deformation and true strain rate induced in the specimen to be independently controlled. The second anvil is moved, preferably through a wedge assembly actuated by the second hydraulic cylinder, during the dwell time between successive deformations. Appropriately positioning the second anvil and then relying on the stop plate rather than the compression piston to abruptly terminate both the travel of this piston during each compressive deformation and hence the strain induced in the specimen advantageously permits this piston to travel at a substantially controlled velocity throughout each entire compressive deformation. As such, a desired relatively high entrance true strain rate can be advantageously maintained in the specimen completely throughout each deformation. Furthermore, by moving the specimen, using the wedge assembly, independently of the compression piston and specifically while that piston is being retracted for a subsequent deformation, dwell time can be advantageously reduced over that associated with conventional mechanical testing systems, including those that utilize wedge stops.

Additionally, my inventive apparatus also has the capability to pass controlled amounts of alternating (AC) electric current through the specimen before, during and/or after each deformation and also to conductively cool the specimen ends from an elevated temperature. This current causes the specimen to self-resistively heat and establish isothermal planes at a desired substantially uniform temperature throughout the work zone of the specimen. By controlling the rates at which the specimen work zone self-resistively heats and thereafter, when desired, conductively cools, the work zone can be dynamically set to experience any one of a wide range of different time dependent temperature profiles. Thus, through accurate control of both specimen deformation and strain rate and work zone temperature, the specimen can undergo not only substantially the same mechanical deformation but also substantially the same thermal processing that will be encountered in a modern medium to high speed multi-stand rolling mill. Consequently, my inventive apparatus can be used to very accurately simulate such a mill.

Furthermore, it is a feature of my invention that even though a specimen undergoes self-resistive heating by virtue of an electrical current that is conducted through various structural components of my inventive test stand as that specimen is being compressed, this stand, including both anvils, nevertheless maintains a very high degree of dimensional stability and hence produces highly reproducible results. In particular, this stand is constructed of materials that possess a relatively high elastic modulus and have a significantly larger cross-sectional area than the specimen. Therefore, the stand is very stiff even while it is compressing a specimen under maximum force. In addition, to minimize any physical expansion of the stand due to electrically induced heating effects, various structural components in the stand are water cooled. Moreover, for plane strain specimens (where the specimen crossection and surface areas are both large as compared to the contact area, i.e. the interface, between each anvil and the specimen), appreciable heating is allowed to occur at the interface between each anvil and the specimen. In this case, heat is also conducted away from the rear surface of both anvils, through water cooling of adjacent components. Operation in this manner advantageously prevents both anvils from appreciably heating and thermally softening while the specimen is being self-resistively heated and also permits the specimen to be thermally processed under controlled conditions and at reasonable programmed heating rates.

BRIEF DESCRIPTION OF THE DRAWINGS

The teachings of the present invention can be readily understood by considering the following detailed description in conjunction with the accompanying drawings, in which:

FIG. 1 graphically depicts a curve that represents both programmed and actual deformation and typically occurs in a typical computer controlled material testing system, which is known in the art and has a servo-hydraulically driven ram, for producing a 40% reduction in specimen thickness using a relatively low and substantially constant true strain rate;

FIG. 2 graphically depicts curves that represent ram travel and programmed and actual deformation, including over-travel, that typically occur in the computer controlled material testing system associated with FIG. 1 whenever that system is simulating a high speed mill stand by producing a 40% reduction in specimen thickness using a relatively high and substantially constant true strain rate;

FIG. 7 graphically depicts a typical position profile of piston rod 509 and anvil 560' shown in FIG. 5 that can be programmably generated by my inventive test stand in order to produce a deformation profile, having illustratively three successive deformations, of a test specimen for use in simulating a final reducing stand in a modern medium-speed three-stand hot mill.

To facilitate understanding, identical reference numerals have been used, where appropriate, to designate identical elements that are common to the figures.

DETAILED DESCRIPTION

Figure 8:
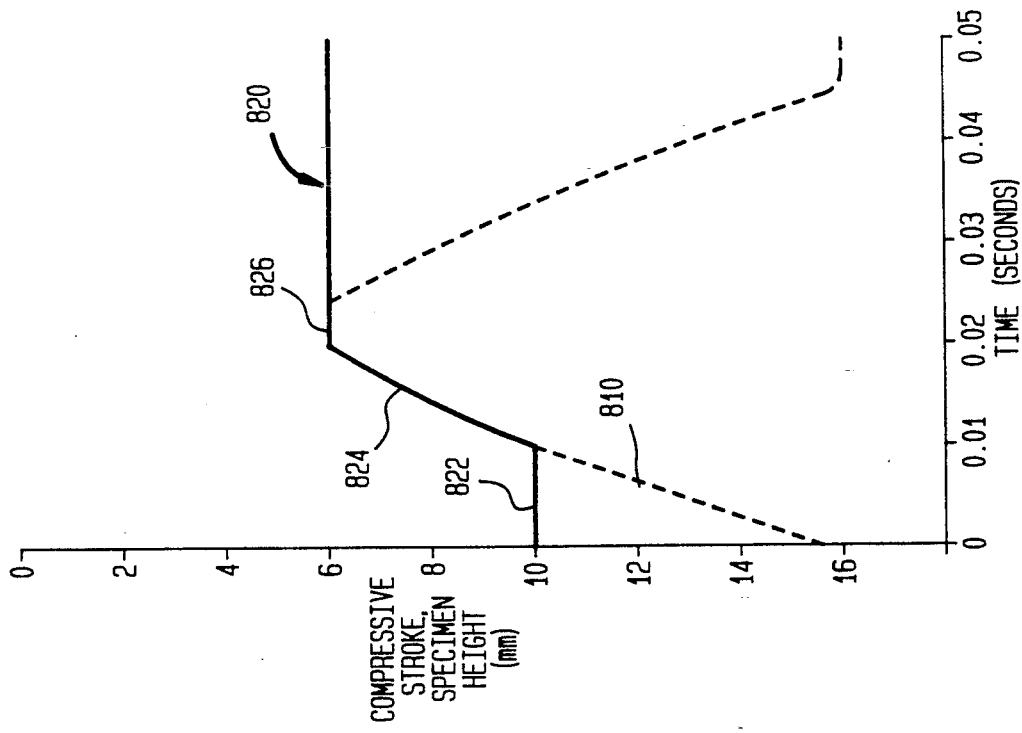
FIG. 8 graphically depicts curves that represent travel of piston rod 509 and both programmed and actual deformation that can be produced by my inventive test stand 500 shown in FIG. 5 whenever that stand is used to simulate a high speed rolling mill by producing a 40% reduction in specimen thickness using the same true strain rate shown in FIG. 2.

After considering the following description, those skilled in the art will clearly realize that the broad teachings of my invention can be readily utilized in conjunction with any one of a variety of dynamic material testing systems for simulating a rolling mill by successively compressing ("hitting") a test specimen. Nevertheless, for purposes of illustration and to simplify the following discussion, I will specifically describe my invention in the context of use with illustratively the GLEEBLE 1500 dynamic thermal-mechanical material testing system (which is hereinafter referred to merely as the GLEEBLE 1500 system) manufactured by the Duffers Scientific, Inc. of Poestenkill, New York (which also owns the registered trademark "GLEEBLE" and is present assignee hereof).

FIG. 1 shows a typical low strain rate deformation curve 100 that occurs in a typical well-known computer controlled material testing system that utilizes a servo-hydraulically actuated ram. In such a system, a specimen is grasped in a fixed mount and then controllably struck ("hit") by a ram mounted, via a rod, to an end of a servo-controlled hydraulic piston. The rate of travel of the ram determines the strain rate of the specimen with the distance through which the ram compresses the specimen determining its deformation.

Curve 100 represents both programmed and actual deformation in such a system with the resulting deformation being comparable to that which would occur in rolling of plate using a single stand mill. This curve shows a 40% reduction in specimen height (from 10 to 6 mm) that occurs at a relatively low but substantially constant low true strain rate. As indicated in curve 100, the specimen is not deformed within regions 110 and 130 and undergoes compression at a true strain rate of 0.4/second in region 120. The ram does not move within regions 110 or 130. The slope of region 120 is the true strain rate, $d\epsilon/dt$. At these low strain rates, constant true strain and final strain can be easily and accurately obtained using a conventional computer controlled servo-hydraulic material testing system. The actual and programmed deformation are identical.

FIG. 2 graphically depicts curves that represent ram travel, and programmed and actual deformation that typically occur in the same conventional computer controlled material testing system but using a relatively high and substantially constant true strain rate. This strain rate is typical of that occurring in a modern medium to high speed multi-stand rolling mill.

As in FIG. 1, a 40% reduction (from 10 to 6 mm) in specimen thickness is being made but at a relatively high substantially constant true strain rate of 40/second. To generate such high strain rates, it is necessary to permit the ram to accelerate before impacting the specimen in order to assure a proper entrance velocity. Stroke travel (and ram movement) both before and after specimen deformation is shown by dashed lines 210 and 215. Solid curve 220 depicts the specimen height. As shown, the ram is accelerating towards the specimen during the first 0.01 second as indicated by line 210 and region 223. Deformation occurs during the next 0.01 second as indicated by region 220 and stops at approximately 0.02 seconds. Region 227 indicates the final specimen thickness with dashed line 215 showing the ram being retracted away from the specimen. As shown, the precision of the resulting deformation deteriorates at high strain rates. This deterioration is caused by excessive strain caused by ram over-travel, specifically over-travel 230. At high ram velocities and owing to the physical forces involved in moving the ram, the servo-hydraulic system is simply unable to maintain a controlled ram velocity throughout the deformation, particularly for small deformations, and then abruptly reduce both the ram velocity and strain rate to zero at the instant the desired deformation is reached.

As the strain rate increases and the specimen deformation accordingly decreases for successive hits, the additional strain caused by ram over-travel becomes relatively large compared to the initial specimen height prior to a hit. Since the final stand(s) of a modern multi-stand rolling mill typically imparts a relatively small deformation but a relatively large true strain rate to rolled strip, the total strain produced in the specimen, including that resulting from ram over-travel, by a conventional material testing system significantly deviates from the strain which would be produced in the rolled strip by each of these stands thereby corrupting the simulated results. If the over-travel is significant as compared to the desired specimen height, then the additional strain imparted to the specimen becomes excessively high. Concomitantly, if the desired deformation is achieved at the instant the ram stops moving, then the ram velocity and hence the resulting true strain rate are both generally too low to accurately simulate actual mill conditions in the specimen.

Furthermore, conventional computer controlled material testing systems with servo-hydraulically actuated rams also tend to suffer from excessive dwell time between successive "hits" and poor end-of-stroke control. Both of these effects further restrict the ability of such systems to accurately simulate actual conditions, particularly in the final stand(s), in modern medium to high speed multi-stand rolling mills.

Figure 4:
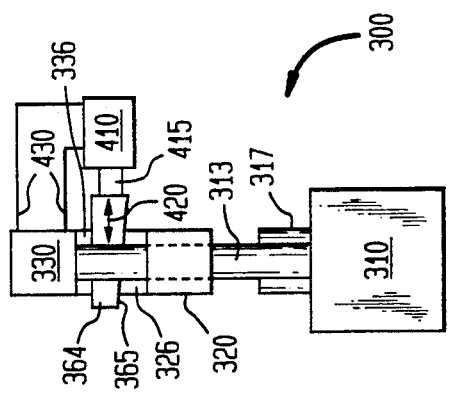
FIG. 4 is a side view of test stand 300 shown in FIG. 3.
Figure 3:
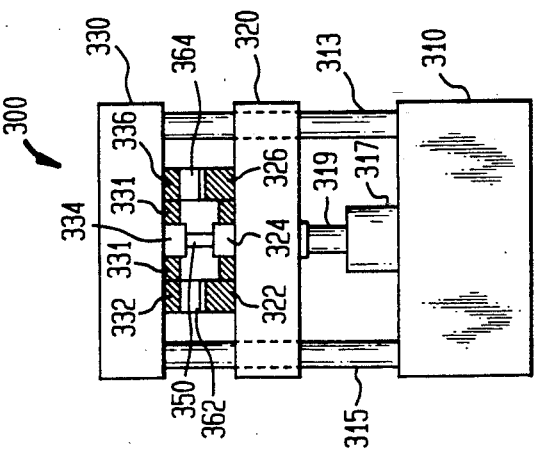
FIG. 3 is a front view of a typical servo-hydraulically driven test stand 300, used in a computer controlled material test system, for imparting compressive deformations to a test specimen and having dual wedge stops as is commonly known in the art.

FIGS. 3 and 4 respectively show front and side views of well-known test stand 300 which attempts to alleviate the above deficiencies inherent in computer controlled servo-hydraulically actuated material testing systems by using dual wedge stops situated between moving and fixed platens to abruptly terminate the specimen strain rate. For ease of understanding, the reader should simultaneously refer to both FIGS. 3 and 4 throughout the following discussion.

In essence, test stand 300 contains lower platen 324 and upper platen 334 each of which contains a well-known ram (not specifically shown). Specimen 350 is placed between the rams and is typically held in place by the ram attached to the upper platen. Upper platen 334 is secured to upper cross head 330 which, in turn, is fixed in position and secured to the ends of support bars 315 and 313; lower platen 324 is secured to lower cross head 320. Piston rod 319 emanating from hydraulic cylinder 317 is connected to a lower surface of lower cross head 320. The support bars extend through the lower cross head and guide its vertical movement. Cylinder 317 is fixedly mounted to base 310 which also secures both support bars. This cylinder is operated by a well-known computer controlled servo-hydraulic control system (not shown) in order to move this cross head along support bars 313 and 315 either upward to compress specimen 350 or downward. Mechanical wedges, which function as stops, are situated between the lower and upper stop blocks, specifically blocks 322 and 332, and 326 and 336 for wedges 362 and 364, respectively. The upper stop blocks are typically connected to suitable strengthening members, such as member 331, as are the lower stop blocks. Each upper stop block is also secured to a bottom surface of upper cross head 330 and has a horizontally oriented base surface that abuts against a horizontal surface of each wedge. Each lower stop block has a horizontal surface that is secured to an upper surface of lower cross head 320 and has an inclined surface complementary to and facing the inclined surface of the wedge, such as surface 365 of wedge 364. Both wedges are identical; the amount of the incline in each wedge is not critical. An illustrative amount may be approximately 17 degrees to yield a 30% inclination. Each wedge, such as wedge 364, is connected via a piston rod to a hydraulic cylinder, such as rod 415 of cylinder 410. Under the control of a separate computer controlled servo-hydraulic system (also well known and not shown), each of these cylinders, such as cylinder 410, extends or retracts its piston rod to move its associated wedge, e.g. wedge 364, between successive deformations along a direction shown by arrow 420, which is transverse to the movement of the lower ram. The wedge and the stop blocks have contact areas with a much larger surface area than the cross-sectional area of specimen 350. In addition, the stop blocks, wedges 362 and 364, base 310, upper and lower cross heads 320 and 330, and upper and lower platens 324 and 334 all have a high elastic modulus and are thus very stiff. Therefore, all these components, particularly the wedges, experience relatively little elastic strain while specimen 350 is being compressed.

In operation, the lower cross head is driven upward by cylinder 317 to continuously cause both rams to compress specimen 350 until the lower stop blocks abut against the inclined surface of the wedges. At this point, the lower cross head immediately ceases any further upward movement thereby abruptly reducing the specimen strain rate to zero. The position of each wedge, i.e. specifically its average thickness between the opposing stop blocks, governs the amount of deformation that will be imparted to the specimen during each "hit". The wedges are appropriately positioned during the dwell time between successive hits. Lower cross head 320 can be lowered somewhat to permit the lower ram to accelerate to a desired entrance velocity upon impacting specimen 350.

While utilizing dual wedges 362 and 364 within test stand 300 advantageously eliminates ram over-travel and its attendant corruption of the simulated results, it disadvantageously requires that, for a constant true strain rate, the ram be decelerated during each hit and that the ram stop at a new position at the end of each successive hit. This, in turn, greatly complicates the programming of such a system in order to achieve a true mill process simulation. Specifically, when programs for use in such a material testing system are written to control the movement of the ram, the program must cause the ram to decelerate while the specimen is being deformed if the true strain rate is to be either held constant or controlled in accordance with the performance of the mill. Since the ram is traveling at a high velocity at the beginning of the hit and the total amount of deformation during a hit may be very small (the ram travel may illustratively be a fraction of a millimeter for some "final" hits), then, owing to response limitations of the system, properly slowing (decelerating) the ram to produce a constant true strain rate (or other programmed rate) in the specimen may be quite difficult to achieve in practice. Furthermore, the changing stop position of the ram for each successive hit further complicates programming the needed ram deceleration and hence significantly increases the difficulty associated with programming a true mill process simulation.

Through the teachings of my invention, which will shortly be discussed with respect to FIGS. 5–8, I have advantageously eliminated the deficiencies associated not only with conventional computer controlled material testing systems that employ servo-hydraulic actuated rams but also with such systems that utilize wedge stops situated between moving and fixed platens.

Specifically, in accordance with particular teachings of my invention, a specimen is oppositely situated between two anvils, each of which is movable with respect to the other. The portion of the specimen that is situated between both anvils and hence will undergo deformation is referred to hereinafter as the "work zone" of the specimen. Both anvils and the specimen are encircled by a stop assembly, illustratively containing a substantially U-shaped cross stop and twin stop bars extending therefrom to a first cross head which, in turn, is mounted to a frame. A first anvil is moved by a first shaft that extends through a second cross head which is also mounted to the frame. This shaft is pushed by a servo-hydraulically actuated piston (the "compression" piston), with the stroke of the shaft being limited by a stop plate, which is also part of the stop assembly, whenever that plate abuttingly engages against the cross stop. The second anvil, which abuts against an end of the specimen and is oppositely situated from the first anvil, is connected to one end of a second shaft which extends through the first cross head. The second shaft can be precisely positioned to incrementally move the specimen by a pre-defined distance towards the compression piston in order to control the exact amount of strain that will be imparted to the specimen by each successive hit. The velocity of the compression piston governs the velocity of the first anvil and hence the strain rate induced in the specimen during its compressive deformation.

Permitting the second anvil to be positionable independently of the stroke distance of the piston advantageously allows the deformation and true strain rate induced in the specimen to be independently controlled. The second anvil is moved, preferably through a wedge assembly actuated by another servo-hydraulically controlled piston, during the dwell time between successive deformations ("hits"). Appropriately positioning the second anvil and then relying on the stop plate rather than the compression piston to abruptly terminate both the travel of the piston during each hit and hence the strain induced in the specimen advantageously permits this piston to travel at substantially a controlled velocity throughout each entire compressive deformation. As such, a desired relatively high entrance true strain rate can be advantageously maintained in the specimen completely throughout each hit. Furthermore, by moving the specimen, using the wedge assembly, independently of the compression piston and specifically while that piston is being retracted for a subsequent hit, dwell time can be advantageously reduced over that associated with conventional mechanical testing systems, including those that utilize wedge stops.

Additionally, my inventive apparatus also has the capability to pass controlled amounts of alternating (AC) electric current through the specimen before, during and/or after each "hit" and also to conductively cool the specimen ends from an elevated temperature. This current causes the specimen to self-resistively heat and establish isothermal planes at a desired substantially uniform temperature throughout the work zone of the specimen. By controlling the rates at which the specimen work zone self-resistively heats and then conductively cools, the work zone can be dynamically set to experience any one of a wide range of different time dependent temperature profiles with relatively little, if any, thermal gradients appearing throughout the work zone. Thus, through accurate control of both specimen deformation and strain rate and work zone temperature, the specimen can undergo not only substantially the same mechanical deformation but also substantially the same thermal processing that will be encountered in a modern medium to high speed multi-stand rolling mill. Consequently, my inventive apparatus can be used to very accurately simulate such a mill.

Figure 5:
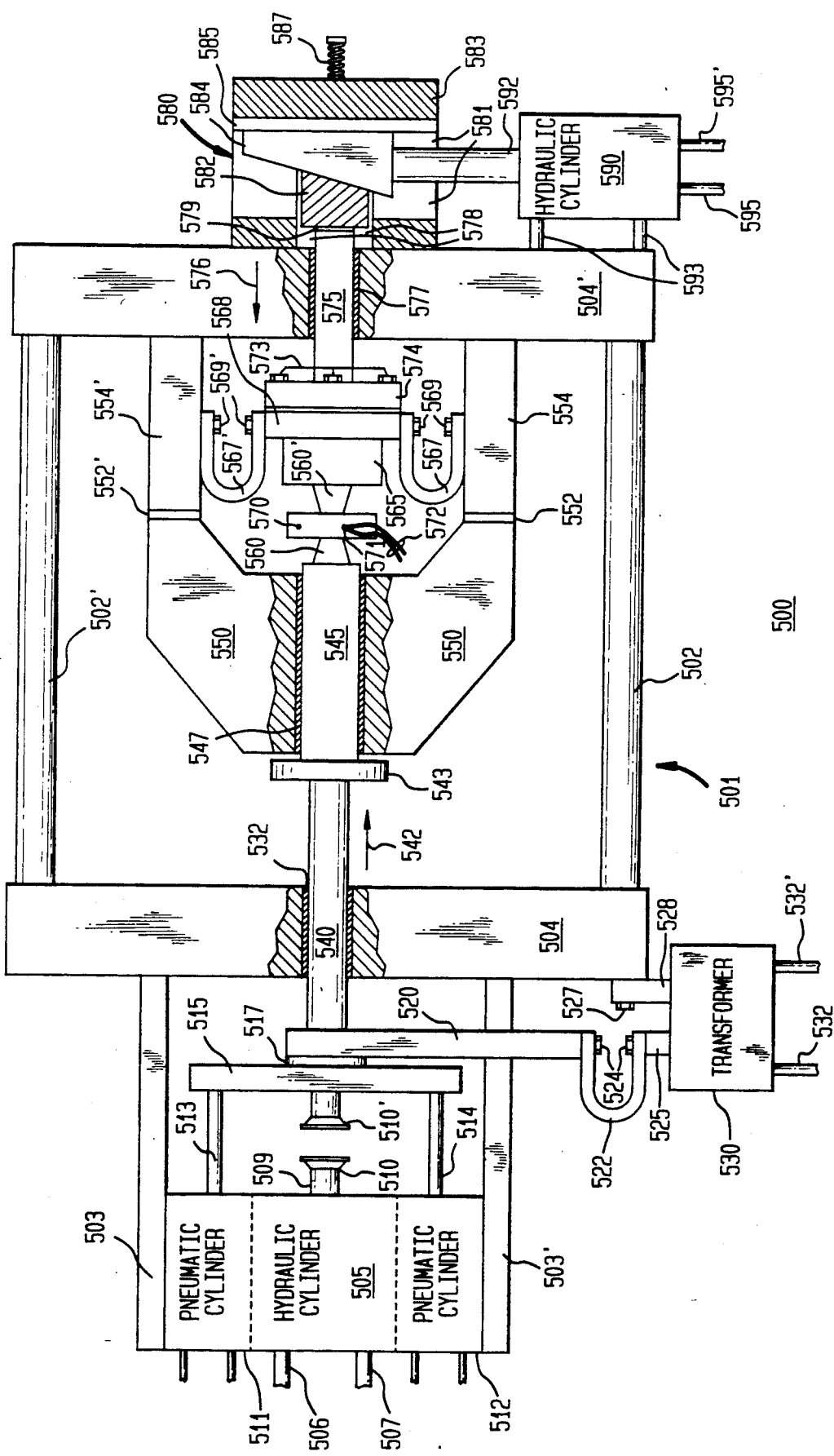
FIG. 5 is a schematic diagram, with partial cut-away views, of a preferred embodiment of my inventive test system and specifically test stand 500 for imparting independently programmed deformation and true strain rate to a test specimen as well as a desired thermal profile thereto.

FIG. 5 is a schematic diagram, with partial cut-away views, of a preferred embodiment of my inventive test system and specifically test stand 500 for imparting independently programmed deformation and true strain rate to test specimen 570 as well as a desired thermal profile thereto. Although this test stand is shown in a horizontal orientation, the stand can be oriented to operate vertically, such as with a compressive stroke occurring in a downward direction, if desired. To simplify the discussion, all references to FIGS. 5-8 of the drawings will assume a horizontal orientation of the stand. Reference should also be made, where indicated during the course of the following discussion, to FIGS. 6A-6C which respectively depict perspective and reverse perspective views of an assembly of wedge yoke 582 and wedge 584 both shown in FIG. 5 and a perspective view of wedge yoke 582 shown in FIG. 6A.

As shown in FIG. 5, test stand 500 contains frame 501 which is formed of two horizontal support columns (bars) 502 and 502' and two cross heads 504 and 504', with opposing ends of these bars fixedly secured in the cross heads. As described below, both these bars and the cross heads are fabricated from conductive materials. In addition, these components are rigidly constructed to withstand the physical forces occurring during compressive deformation of the specimen. Furthermore, each of these and other components, as discussed below, in stand 500 has a high elastic modulus so as to exhibit relatively little elastic strain during specimen deformation. Stand 500 also contains hydraulic cylinder 505 and pneumatic cylinders 511 and 512 all mounted within a common block of material and secured, via braces 503 and 503', to frame 501 and specifically cross head 504. All these cylinders operate bi-directionally. Piston rods 513 and 514 of pneumatic cylinders 511 and 512 are rigidly attached to cross bar 515. This cross bar is rigidly connected, using non-conductive fasteners, through insulating plate 517 to conductor 520 which, in turn, abuts against and is securely connected to one end of conductive shaft 540. Each of these fasteners is typically formed of a high strength bolt with an insulated sleeve situated around its shank, an insulated washer at its head and a back-up washer located between the insulated washer and the head. Shaft 540 rides within and is guided by electrically insulating bearing (sleeve) 532 extending through cross head 504 and lining a hole made therethrough. This bearing is illustratively a TEFLON material composite bearing such as a DIXON type CJ bearing manufactured by Dixon Industries Corporation of Bristol, Rhode Island ("TEFLON" is a registered trademark of E.I. Du Pont de Nemours and Company in Wilmington, Del.; "DIXON" is a trademark of Dixon Industries Corporation). As such, shaft 540 is mechanically connected to and moved by cross bar 515 but is electrically insulated from it. The opposite end of shaft 540 abuts against conductive stop plate 543. This stop plate is connected to one end of extension shaft 545. This extension shaft rides within and is guided by bearing 547 which extends through U-shaped cross stop 550. Bearing 547 may also be a DIXON type CJ bearing, though this particular bearing need not be electrically insulating. This shaft is also rigidly connected at its opposite end to anvil 560. This bearing lines a corresponding hole extending axially through the cross stop. The stop plate has a significantly larger diameter than this hole in the cross stop. Piston rod 509, couplers 510 and 510', shafts 540 and 545, stop plate 543, and anvil 560 are all coaxially aligned. The portion of specimen 570 situated between anvils 560 and 560' is the work zone.

With test stand 500 as thusfar described, pneumatic cylinders 511 and 512 are initially set, prior to commencing movement of shaft 509 to compress specimen 570, to appropriately distend piston rods 513 and 514 to move cross bar 515 in the direction shown by arrow 542 such that anvil 560 establishes firm abutting contact with one side of specimen 570. This assures that a low resistance current path will occur between conductor 520 and one side of specimen 570 and specifically through shaft 540, stop plate 543, extension shaft 545 and anvil 560. Cylinders 511 and 512 are operated by appropriately controlling a source of high pressure air (typically on the order of approximately 1 to 6 bar, i.e. 15 to 90 psi) supplied through well-known air regulators (not shown) in order to each provide between 50-400 pounds (approximately 220 to 1800 newtons) of force.

Hydraulic cylinder 505 provides the necessary compressive force to anvil 560 to deform specimen 570 and imparts the necessary speeds to that anvil to obtain desired strain rates in the specimen. Piston rod 509 is connected to coupler 510. Coupler 510' is securely attached, through a short shaft, to cross bar 515. Both couplers have flat faces and are arranged such that these faces are opposing each other. Specimen compression begins when piston rod 509 has sufficiently moved coupler 510 such that its flat face abuttingly engages the corresponding face of coupler 510'. The resulting motion of both couplers is in the direction shown by arrow 542. Piston rod 509 can be retracted into cylinder 505 in order to permit coupler 510 to freely travel over a finite distance and accelerate prior to striking coupler 510'. Higher pressure pipes 506 and 507 are connected to inlet and outlet ports of cylinder 505. This cylinder is controlled by a well-known hydraulic servo-control value (not shown) and computer driven control circuits such as those typically found in the GLEEBLE 1500 system manufactured by the present assignee. Inasmuch as servo-control values and associated computer control circuits are all very well known in the art, they will not be discussed any further herein. Pneumatic cylinders 511 and 512 provide a much lower force than hydraulic cylinder 505. In this regard, the combined force of the pneumatic cylinders may be approximately 800 pounds (approximately 3500 newtons) with the hydraulic cylinder providing as much as approximately 18,000 pounds (approximately 8.3 metric tons) of force. The combined effect of hydraulic and pneumatic cylinders 505, 511 and 512 is to move anvil 560 in the compressive direction at high speed and with high force but in the tension direction (opposite to that shown by arrow 542) at relatively low speed and with a low force.

Specimens to be tested by stand 500 in plane strain are generally rectangular in cross-section and typically vary in thickness from 10 to 40 mm. These specimens will also vary between 14 to 100 mm in width and from 20 to 200 millimeters in height. To assure a substantially uniform temperature gradient (i.e. with very little or no temperature gradients) occurs across the work zone of each plane strain specimen (i.e. the portion of the specimen situated between the anvils) during heating, each of these specimens generally has surface areas for each of two opposing surfaces and a crosssectional area that are each significantly larger than the contact area between each anvil and each of these surfaces. The current flow required to heat metallic specimens of these sizes and at heating rates equal to or exceeding rates experienced in modern medium to high speed rolling mills will vary from a few hundred amperes to approximately 22,000 amperes. This electrical current is provided by transformer 530 which provides a source of high current at a low voltage. Though not critical, the transformer should possess a 440 volt, single phase 75 kVA primary with a 5.7 to 10 volt paralleled secondary, preferably controlled by a tap switch, and a 50 or 60 Hz operating frequency. The short circuit output current should be on the order of 50 kA or more. The secondary winding of the transformer is typically formed of one or two turns of a heavy copper casting. By varying the turns ratio of the transformer in finite increments through the tap switch, specimens of different sizes and shapes can be readily heated. Such a transformer is the model G4475NS61S manufactured by Kirkhof Transformer of Grand Rapids, Mich. Leg 528 of the secondary of transformer 530 is rigidly connected to frame 501 and is secured, via bolt 527, to cross head 504. The other leg, i.e. leg 525, of the transformer is securely connected, via bolts 524, to rolling flexible conductor 522. This conductor, typically 1.3 cm (approximately 0.5") in total thickness, is formed of a series of parallel copper laminations. Rolling flexible conductors 567 and 567' are identically formed. Leads 532 and 532' are connected to the primary of transformer 530 and carry current thereto from a well-known single current supply (not shown). The current supply is a suitable single phase SCR (silicon controlled rectifier) based thermal control system as is commonly used in the GLEEBLE 1500 system.

Stop bars 554 and 554' are rigidly attached to cross head 504' and, via insulating spacers 552 and 552', to cross stop 550, all of which are contained within a stop assembly. This assures that the cross stop is mechanically connected through the stop bars to cross head 504' but is electrically insulated therefrom. To complete the series electrical current path through specimen 570, rolling flexible conductors 567 and 567' are rigidly attached, via fasteners 569 and 569', to stop bars 554 and 554' and to conductor plate 568. The left side of this plate is secured to anvil support 565 to which anvil 560' is mounted. This anvil abuts against one end of speciment 570. To measure the compressive force or load applied to speciment 570, load cell 574 is situated between the right side of conductor plate 568 and one end of wedge shaft 575. Separate fiber glass washers are situated on both sides of the load cell to insulate it and prevent electrical current from flowing between the load cell and either conductor plate 568 or wedge shaft 575. The load cell is secured along its perimeter by well-known insulated bolts 573 (of which only three are shown for simplicity) extending through both the fiberglass washers and the load cell into conductor plate 568.

Figure 6C:
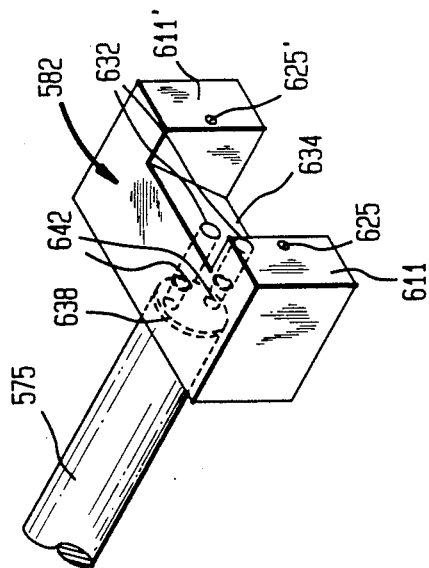
FIG. 6C depicts a perspective view of wedge yoke 582 shown in FIG. 6A.
Figure 6B:
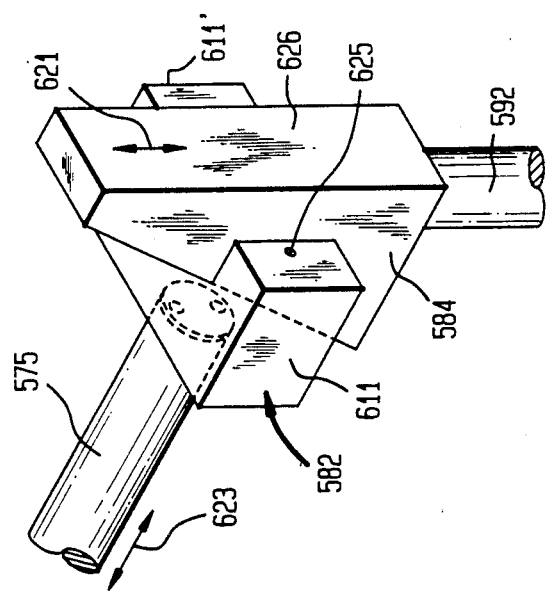
FIGS. 6A and 6B respectively depict perspective and reverse perspective views of an assembly of wedge yoke 582 and wedge 584 both shown in FIG. 5.
Figure 6A:
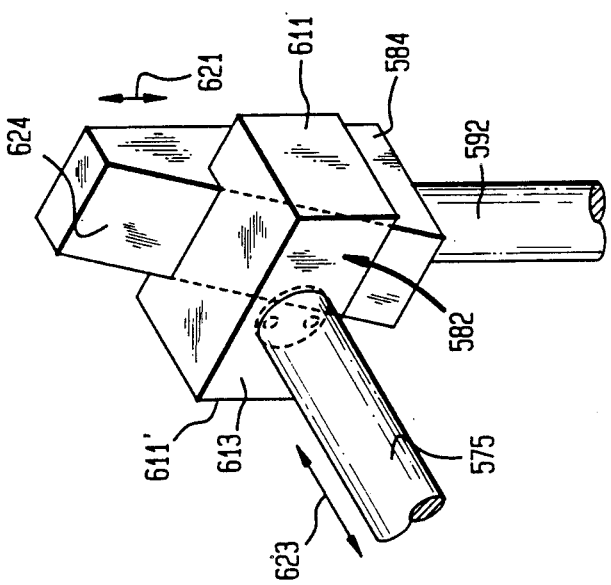

Wedge shaft 575 extends from load cell 574 through cross head 504' and runs within and is guided by insulated bearing 577, which may also be a DIXON type CJ bearing. This bearing lines a hole extending completely through this cross head. To further reduce electrical fields near the load cell, wedge shaft 575 is connected to wedge yoke 582 through insulated fiberglass washer 579. Wedge assembly 580 is shown in a cross-section cutaway view for clarity in viewing the action of wedge and wedge yoke. The wedge yoke is securely fastened to wedge shaft 575, as shown in FIGS. 6A-6C, by two insulated bolts (not shown) that extend through rear surface 613 of the wedge yoke. These bolts have insulation situated around their shanks and insulated washers positioned under their heads. These bolts extend through countersunk holes 632 in wedge surface 634, through holes 642 (only one of which is specifically shown) which extend through the body of the wedge yoke, past recess 638 (which accommodates fiberglass washer 579—not specifically shown in this figure) and into an end of wedge shaft 575. As shown, wedge yoke 582 has wedge surface 634 which is inclined on the order of illustratively 17 degrees (to yield approximately a 30% inclination) with respect to the vertical axis of the yoke and is situated between two opposing tongues 611 and 611' that extend in parallel outward of wedge surface 634. Surface 634 abuttingly engages with and slides against complementary shaped surface 624 situated on wedge 584. As shown in FIGS. 5 and 6A-6B, wedge 584 is connected to piston rod 592 which, through hydraulic cylinder 590, moves the wedge vertically up or down. This cylinder is secured to cross head 504' by rigid braces 593. This vertical movement, in the direction shown by arrow 621, when translated through the sliding action of the wedge and wedge yoke causes shaft 575 to move in the direction shown by arrow 623 which, in turn, causes load cell 574, conductor plate 568, anvil 560' and ultimately specimen 570 mounted thereto to move either to the left as shown by arrow 576 or to right in a direction opposite to that shown by this arrow. Anvil 560', anvil support 565, conductor plate 568, load cell 574, shaft 575, washer 579 and wedge yoke 582 are all coaxially aligned with themselves and with components, e.g. anvil 560, through which compressive force from cylinder 505 is transmitted to specimen 570.

With reference to FIG. 5, hydraulic cylinder 590 which actuates piston 592 generally provides the same force as that provided during compression testing by cylinder 505, i.e. illustratively on the order of 8.3 metric tons. High pressure pipes 595 and 595' route hydraulic fluid to an inlet port and from an outlet port of cylinder 590. This cylinder is controlled by a well-known hydraulic servo-control value (not shown) and computer driven control circuits such as those typically found in the GLEEBLE 1500 system manufactured by the present assignee. With wedge 584 possessing approximately 17 degrees of slope (again to yield approximately a 30% inclination), wedge shaft 575 only moves approximately 30% as fast and 30% as far as does piston rod 592. As such, wedge 584 multiplies the force of cylinder 590 and in essence provides a very still support to anvil 560'. Accordingly, any attempt to push anvil 560' during compression testing in a direction opposite to that shown by arrow 576 is met with mechanical resistance that is much greater than that which is provided by cylinders 505, 511 and 512. Furthermore, the path of mechanical resistance to cross head 504 is short and is through wedge shaft 575, wedge yoke 582, wedge 584 and wedge guide 583 which is bolted securely (though not specifically shown as such) to cross head 504'. Inasmuch as the cross-sectional area of all these components is relatively large, the stress (force/unit area) that occurs therein is kept fairly low. This, in turn, limits the strain in these components to a very small value even at the maximum force provided by hydraulic cylinder 505. Consequently, anvil 560' can be carefully and rapidly positioned by hydraulic cylinder 590 and will thereafter remain in that position even while cylinder 505 is compressing specimen 570 by moving anvil 560 at a high speed and with a high force. Furthermore, the elastic modulus of these components is high which further reduces the elastic strain that occurs in these components during compression testing of specimen 570.

Wedge assembly 580 also includes two wedge guide plates, wear plate 585 and return springs 587. The wedge guide plates are mirror images of each other and are positioned atop one another. With this in mind and inasmuch as only one guide plate, i.e. plate 583, is shown in FIG. 5 so as to fully expose wedge 584 and wedge yoke 582 within assembly 580, the following discussion will not specifically address the other guide plate. As shown, groove 581, equal in width to approximately one half of the thickness of wedge 584 plus a suitable clearance amount, is cut vertically across wedge guide plate 583. Wedge 584 runs vertically within this groove. Rear surface 626 of the wedge slides against wear plate 585 (which extends out of the plane of the drawing) that is mounted to both guide plates. Groove 578, which is deeper and narrower than groove 581, is cut horizontally within guide plate 583 and perpendicular to groove 581. Groove 578 has a depth equal to approximately one half the width of wedge yoke 582 plus a suitable clearance amount. A tongue of wedge yoke 582, illustratively tongue 611' (see FIGS. 6A-6C), runs within and is guided by groove 578 shown in FIG. 5. As such, both guide plates collectively provide grooves within which the wedge yoke tongues 611 and 611' (see FIGS. 6A-6C) are guided for horizontal movement. Heavy return springs 587 (only one of which is shown in FIG. 5) are connected to the opposing tongues of wedge yoke 582 through threaded holes 625 and 625' shown in FIGS. 6B and 6C. As shown in FIG. 5, these return springs are both compressed against the guide plates and therefore exert a force onto the wedge yoke that pulls the yoke and wedge shaft 575 in a direction opposite to that shown by arrow 576 so as to maintain both the wedge and wedge yoke in intimate contact with each other. These return springs have bolts that extend through the wedge guide plates and wear plate 585 into threaded holes 625 and 625' as shown in FIG. 6C, located in opposing tongues 611 and 611' of wedge yoke 582. As discussed, wedge 584 is not moved while each compressive hit is being made to specimen 570 but rather only during the dwell time between successive hits and specifically while piston rod 509 is being retracted.

Advantageously, wedge assembly 580 can be designed to minimize any force transmitted to cylinder 590 during each compressive deformation of the specimen. In particular, abutting surfaces 634 on the wedge yoke and 624 on the wedge (see FIGS. 5 and 6A-6C), and surface 626 and the corresponding surface on wear plate 585 can each be roughened, such as through sandblasting or other well-known techniques, to provide relatively high amounts of sliding friction therebetween. As such, most of the force transmitted through the wedge during each compressive deformation of the specimen will be expended to overcome the sliding friction existing between these surfaces rather than being applied through piston rod 592 to cylinder 590. Since the wedge is moved while only the pneumatic cylinders are exerting a force onto the specimen and particularly during the dwell time existing between successive hits, this sliding friction can be easily overcome by cylinder 590 and hence the wedge can be freely moved to increase the strain that will be imparted to the specimen during the next successive hit. Owing to the substantially greater force produced through by hydraulic cylinder 590 wedge assembly 580 than the combined force produced by both pneumatic cylinders 511 and 512, piston rods 513 and 514 emanating from these pneumatic cylinders are simply pushed back (i.e. forcibly retracted) by movement of the wedge assembly in the direction shown by arrow 576. Consequently, as the wedge assembly incrementally moves specimen 570 to the left by a distance, then the force exerted by the wedge assembly through the specimen simply causes piston rods 513 and 514 to retract into the pneumatic cylinders by the same distance. However, the opposing force that is being simultaneously exerted onto the specimen by the pneumatic cylinders is sufficient to maintain good electrical and thermal contact between both anvils 560 and 560' and specimen 570 and thereby permits heating current to simultaneously flow therethrough. Maintenance of this contact permits the work zone of the specimen to self-resistively heat or conductively cool, as desired, between successive hits.

Stop plate 543, which also forms part of the stop assembly and is mounted to an end of shaft 545, in conjunction with cross stop 550, accurately controls the strain rate imparted to the specimen during each compressive deformation. Specifically, shaft 540, when moved in the compressive direction indicated by arrow 542, abruptly halts its compressive stroke when stop plate 543 impacts against cross stop 550. Inasmuch as the cross stop is rigidly secured through stop bars 554 and 554' to cross head 504', stop plate 543 will immediately stop any forward progress of anvil 560 even if it is compressing specimen 570 at the maximum force supplied by cylinders 505, 511 and 512. Stopping the anvil in this manner assures that the anvil will always stop in an exact physical position, at which the true strain rate imparted to the specimen will abruptly drop to zero, regardless of the speed of the anvil in the compressive direction or the force applied to it by cylinders 505, 511 and 512. Inasmuch as the stop plate has a significantly larger diameter than the hole through the cross stop and is relatively thick, the stop plate will not deform when it impacts against cross stop 550. This same stopping procedure is used with each successive hit regardless of the number of times specimen 570 is to be successively compressed.

If specimen 570 is to undergo thermal processing in order to establish a time dependent thermal profile therein, it is necessary to synchronize the desired thermal operation (i.e. the so-called "thermal program") which self-resistively heats and conductively cools the specimen at specified heating and cooling rates to the mechanical operation of the test stand, i.e. the so-called "deformation program". The latter program imparts a pre-defined deformation profile to the specimen.

As discussed above, the specimen is heated by passing a controlled amount of electrical current therethrough. During one half of a cycle of applied AC power, this current flows from transformer 530, leg 525 and rolling flexible conductor 522; through conductor 520, shaft 540, stop plate 543, extension shaft 545 and anvil 560 to one side of specimen 570. This anvil is maintained in good electrical contact with the specimen while it is being deformed. To provide this, as discussed above, pneumatic cylinders 511 and 512 supply a suitable force through cross bar 515 to shaft 540 and hence to anvil 560. This force is applied regardless of the action of hydraulic cylinder 505. This force squeezes the specimen against anvil 560' which is securely held in place by wedge assembly 580. As such, the specimen can not move between the anvils unless the wedge assembly permits such movement. As long as stop plate 542 is not abutting against cross stop 550 but rather is situated apart therefrom, the force applied by the pneumatic cylinders is supported only by specimen 570.

During this half cycle, the return path of the electrical current flowing through specimen 570, is initially through anvil 560', anvil support 565 and conductor plate 568. This plate splits the current flow through rolling flexible conductors 567 and 567' (each of which carries approximately one half of the current flow). The current then flows through stop bars 554 and 554' and recombines in cross head 504'. From there, the current splits once again with approximately one half of the current flowing in each of support columns 502 and 502'. Inasmuch as these columns are secured to cross head 504, the current will recombine in this cross head and flow through leg 528 back to transformer 530. Current flow will reverse its direction at successive cycles of applied AC power. Heating current flows through both support columns in the same direction but generates magnetic flux lines of opposing polarity in the specimen. Both support columns are identically sized, such that an approximately equal amount of heating current flows through each column. In addition, these columns are appropriately positioned relative to specimen 570 such that the magnetic fields generated by current flow through both columns are balanced and effectively cancelled in the work zone of the specimen. This advantageously eliminates induced current flow in the work zone of the specimen that would otherwise result from these fields. By doing so, substantially all non-uniform current flow throughout the cross-section of the specimen work zone and non-uniform heating that would otherwise result from any such induced current flow are also eliminated thereby assuring that any thermal gradients which appear in the work zone will be very small. Furthermore, cancellation of these fields also substantially eliminates any forces from operating on the specimen that would otherwise result from high current flowing through these columns. In addition, the cross-section and conductivity of all the current carrying components are chosen such that the entire current path, apart from the specimen, presents a very low electrical resistance and hence a very low voltage drop even at currents on the order of 10 kA or more. By keeping the electrical losses of the current path quite low and inasmuch as the resistance of both the specimen and the interface between the specimen and each anvil are relatively high, most of the electrical power supplied by transformer 530 will be delivered to the specimen. Accordingly, most of the heat caused by this current will be generated in specimen 570. Furthermore, since the mechanical size and ductility of materials change during heating, columns 502 and 502', conductor 520, shafts 540 and 545, anvil support plate 565 and conductor plate 568 all contain internal cooling passages, preferably for use with water cooling. A sufficient volume of water is pumped through these components at an appropriate rate to assure that the temperature at each interface between the anvil and the specimen does not rise more than approximately 20 degrees C. during heating. This advantageously minimizes any physical expansion of these components and prevents both anvils from softening. Accordingly, a desired final specimen thickness will be accurately reproducible by test stand 500 throughout a series of separate tests.

The temperature of the specimen work zone is measured by thermocouple 571 which is percussion welded to the specimen. Leads 572 which emanate from the thermocouple are connected to a thermal control system (not shown), such as that utilized on the GLEEBLE 1500 system. In essence, the temperature of the specimen work zone is compared to a programmed temperature value to generate an error signal within the thermal control system in order to vary the output of transformer 530. The output is varied by an amount sufficient to drive the temperature of the work zone of the specimen to the programmed value as a function of time. Either a well-known pyrometer or other temperature measuring device may readily be substituted for the thermocouple, if desired. The temperature is controlled, as a function of time, and is synchronized to the programmed mechanical deformation of the specimen. By simultaneously controlling both the work zone temperature as well as its physical deformation, my inventive test stand 500 can accurately simulate the action of modern medium to high speed multi-stand rolling mills in the specimen.

To illustrate the deformation profiles that can be typically generated by my inventive test stand 500, FIG. 7 graphically depicts a typical position profile of piston rod 509 and anvil 560' shown in FIG. 5 that can be generated by this test stand so as to produce a deformation profile containing illustratively three successive deformations of test specimen 570 for use in simulating a final reducing stand in a modern medium-speed three-stand hot mill. The amount of each deformation is typical of that which occurs in each corresponding stand of such a mill. For ease in understanding, reference should be simultaneously made to both FIGS. 5 and 7 throughout the following discussion.

As depicted, curve 710 shows the position of piston rod 509 as a function of time; curve 750 shows the simultaneous position of anvil 560', also as a function of time. A sequence of illustratively three deformations is shown. Regions 711 and 773 indicate the intial positions of piston rod 509 and anvil 560', respectively. The position of anvil 560' at the maximum compression of the specimen, i.e. as permitted by stop plate 543 and cross stop 550, is indicated by line 740. The deformations depicted in FIG. 7 begin by advancing piston rod 509 in the direction indicated by arrow 542. Region 711 is a dwell region during which the piston does not move. Movement begins at slightly rounded region 713 which represents the acceleration of the piston to a desired velocity. Due to the inertia of the piston, this region can not be square; otherwise an infinite force would be required to bring the piston immediately up to speed. Thereafter, coupler 510 contacts coupler 510' causing shaft 540 and anvil 560 to move to the right and compress specimen 570 at a constant strain rate throughout a lower portion of region 715. The velocity of the anvil is given by the slope of region 715. This compression continues until stop plate 543 contacts cross stop 550, as indicated by point 717, at which point the strain rate in the specimen abruptly drops to zero and no further compression occurs during this deformation. At the conclusion of the deformation indicated by line 740, the specimen thickness is given by distance 761. Shortly thereafter, at point 719, piston rod 509 is accelerated in a reverse direction and is thereafter retracted back to its starting position as indicated by point 721. During subsequent dwell time 723 piston rod 509 does not move; however, wedge assembly 580, actuated by cylinder 590, moves anvil 560' incrementally to the left, as indicated by arrow 576 and specifically through the difference between distances 761 and 763, in preparation for the second deformation of the specimen. As such, the stop plate will also be moved to the left of the cross stop (in the direction shown by arrow 576) by the same difference. Accordingly, the final strain that will be produced in the specimen by the second deformation will also be equal to this difference. The second deformation begins with piston rod 509 being accelerated and then travelling through region 725, with a faster velocity than it had during region 715. Actual compression of the specimen occurs during the lower portion of region 725. This compressive deformation abruptly halts when the stop plate once again abuts against the cross stop and produces a final thickness indicated by dimension 763. The piston is then retracted and the wedge assembly moves anvil 560' incrementally to the left, by the difference between distances 767 and 763, and the piston is thereafter once again accelerated and so on for the third deformation. During the third deformation, the piston compresses the specimen with a larger velocity, as indicated by the slope of region 735, than during either the first or second deformations. Similarly, the specimen is actually compressed only during a lower portion of region 735. The final specimen thickness at the conclusion of the three deformations is indicated by distance 767. As discussed above, while anvil 560' is being incrementally moved a desired distance to the left by wedge assembly 580, piston rods 513 and 514 of pneumatic cylinders 511 and 512 are simultaneously pushed back to the left by an equal distance. Nevertheless and again as discussed above, the pneumatic cylinders continue to exert a sufficient force through shaft 540 and the specimen to assure that a low resistance electrical and thermal path continually exists between conductor 520 and the specimen in order to allow the specimen to self-resistively heat (or conductively cool). The dwell times shown in FIG. 7 arise inasmuch as piston rod 509 is being cycled at less than its maximum rate.

As should now be evidently clear, the velocity of piston rod 509 and the specimen strain rate can be set independently of the final strain of the specimen. The piston velocity and specimen strain rate is determined, inter alia, by the free travel of the piston rod, while the specimen strain is determined by the total incremental movement of anvil 560' through wedge assembly 580. Inasmuch as the thickness and changes in thickness of the specimen are known values, either the velocity of the piston or the strain rate of the specimen may be directly programmed as desired control values into the test program executed by the computer that controls test stand 500 and specifically cylinder 505. In addition, given these known values and inasmuch as this computer also controls cylinder 590, either the specimen thickness or the specimen strain at desired specimen thicknesses may also be directly programmed as desired control values into this computer. The computer that operates the GLEEBLE 1500 system can be readily programmed to function in this manner in addition to providing an additional output axis to control movement of the wedge.

With the above operation in mind, the final thickness of the specimen, regardless of the number of hits it experiences, can be precisely programmed. Similarly, the entrance strain rate can also be precisely programmed. During operation, these values essentially remain independently controllable. Furthermore, the motion of piston rod 509 can be programmed to alter its velocity while it is compressing the specimen and/or during the time shaft 540 is forcing stop plate 543 against cross stop 550. In this case, test stand 500 could include an appropriate device to measure the speed of anvil 560. Doing this would not only permit a desired strain rate to be produced throughout each deformation but would also allow positionally controlled variations to be produced in the strain rate at any time during each deformation.

FIG. 8 graphically depicts curves that represent travel of piston rod 509 and both programmed and actual deformation that can be produced by my inventive test stand 500 shown in FIG. 5 whenever that stand is used to simulate a high speed rolling mill by producing a 40% reduction in specimen thickness (illustratively from 10 to 6 mm) using the same substantially constant true strain rate shown in FIG. 2. As specifically shown in FIG. 8, dashed curve 810 depicts movement of piston rod 509; while solid curve 820 depicts specimen height.

During region 822, lasting 0.01 seconds, the piston rod is accelerating in free travel towards anvil 560 to the appropriate entrance velocity. Deformation occurs during the next 0.01 second as indicated by region 824 and stops at approximately 0.02 seconds. Region 826 indicates the final specimen thickness, shortly after that is attained the piston rod is retracted. Inasmuch as the movement of anvil 560 abruptly stops when stop plate 543 impacts against cross stop 550 (see FIG. 5), the specimen strain rate instantly decreases to zero when the desired deformation is reached and no over-travel advantageously results. Thus, both the programmed and actual deformation remain the same. As can be seen in FIG. 8, anvil 560 has maintained a substantially constant strain rate entirely throughout the deformation, even at relatively high anvil velocities.

Clearly, wedge assembly 580 shown in FIG. 5 can be replaced with a second hydraulic cylinder (or other well-known high force actuator) which directly drives shaft 575 to the left in a direction that would compress specimen 570 from the right. The piston rod from this cylinder (or other actuator) must exhibit a high degree of stiffness otherwise anvil 560' would likely move to the right during a compressive deformation. Inasmuch as hydraulic fluid is typically oil, it has some compressibility. As such if such a cylinder was used, the resulting support for anvil 560' would not be as rigid as through wedge assembly 580 and specifically through abutting wedge yoke 582 and wedge 584, both of which are relatively solid objects that exhibit relatively little elastic strain during compression testing. Although hydraulic fluid is used within cylinder 590, the force imparted to cylinder 590 through the wedge is relatively minimal due to mechanical leverage occurring between wedge yoke 582 and wedge 584 and the sliding friction among the wedge yoke, the wedge and wear plate 585, all of which are shown in FIG. 5.

In addition, wedge assembly 580 could be connected to stop plate 543 in which case the position of anvil 560' would be fixed by cross head 504'. In this case, the stroke distance of piston rod 509 would be changed, i.e. increased, by the amount of strain to be induced into the specimen at each deformation. Placing the wedge assembly in this location would unfortunately complicate the programming of the movement of piston rod 509 by tying the specimen strain and strain rate together through the programmed movement of this piston. Moreover, a wedge assembly connected to stop plate 543 would require a wedge yoke and two separate wedges rather than a wedge yoke and one wedge and hence be somewhat more complicated than the assembly described above.

Furthermore, although the stop assembly has been described as containing stop plate 543, U-shaped cross stop 550, insulating spacers 552 and 552', and stop bars 554 and 554', this stop assembly can readily be fabricated using any one of a number of different configurations, and particularly if a cross stop is used, any one of a wide variety of differently shaped cross stops than that shown in FIG. 5. Functionally, this assembly, regardless of its configuration, needs to abruptly stop the compressive stroke of piston rod 509 while exhibiting minimal elastic strain under the maximum compressive force provided by test stand 500. Moreover, if this assembly is to carry heating current, then provisions need to be made to this assembly, such as forced cooling, to assure that its thermal expansion due to self-heating is kept as low as possible.

Although a single preferred embodiment which incorporates the teachings of my present invention has been shown and described in detail herein, those skilled in the art can readily devise many other varied embodiments that still incorporate these teachings.

I claim:

1. In a material testing system, apparatus for controllably deforming a specimen comprising:

force producing means, having a first actuator and mounted to a fixed frame, for controllably generating a mechanical force along a first pre-defined direction;

first and second deforming means for compressively deforming a specimen so as to generate a compressive deformation therein, wherein said first and second deforming means abuttingly engage with corresponding opposing sides of said specimen while the specimen is being deformed;

force transferring and stopping means, situated in abutting engagement with said first deforming means, for moving said first deforming means, in response to said force, along said first pre-defined direction so as to compressively deform said specimen and for terminating further movement of said first deforming means as soon as said first deforming means has compressed said specimen by a pre-determined amount; and moving means, having a second actuator and coupled to said second deforming means and mounted to the fixed frame, and operative in response to the second actuator, for moving said specimen and said first and second deforming means by the pre-determined amount and in a second direction opposite to the first pre-defined direction prior to commencement of said compressive deformation, wherein said moving means experiences substantially no movement in said first pre-defined direction while said specimen is being compressively deformed;

whereby strain rate and final strain induced in the specimen during said compressive deformation are respectively and substantially independently determined by velocity of said force transferring and stopping means along said first direction during said deformation and a distance that said moving means is moved in said second pre-defined direction prior to said deformation.

2. The apparatus in claim 1 wherein the moving means comprises:

a wedge shaft connected at one end to said second deforming means and extending in said first direction therefrom;

a wedge having a first inclined surface;

a wedge guide fixedly connected to said frame for guiding movement of said wedge along third and fourth directions, said third and fourth directions being opposite to each other and substantially perpendicular to said first and second directions;

a wedge yoke connected to said wedge shaft at a second end thereof and having a second inclined surface complementary to said first inclined surface for slidably engaging with said first inclined surface so as to move said wedge yoke in either said first or second directions as said wedge yoke is moved in said third or fourth directions, wherein said wedge yoke moves at a pre-defined proportion of distance and rate at which said wedge moves while in sliding engagement therewith; and wherein the second actuator is connected to said wedge at one end thereof for controllably moving said wedge through a desired distance in either said third or fourth directions.

3. The apparatus in claim 2 wherein said wedge guide comprises:

a first groove situated along said third and fourth directions for guiding said wedge for movement therealong; and a second groove intersecting with and substantially perpendicular to said first groove for guiding said wedge yoke along said first and second directions in response to movement of said wedge.

4. The apparatus in claim 3 wherein said wedge guide further comprises a wear plate situated between a rear surface of said wedge and an opposing parallel surface of said wedge guide and fixedly secured to said wedge guide for providing a wearing surface for slidable engagement with the rear surface of the wedge.

5. The apparatus in claim 4 wherein the rear surface of the wedge and the wearing surface of the wear plate, and the first and second inclined surfaces are roughened so as to provide increased sliding friction therebetween.

6. The apparatus in claim 5 wherein said wedge yoke comprises: first and second tongues, each of which is situated on one side of said inclined surface and both of which extend in a parallel direction outward therefrom; and said wedge guide comprises first and second return springs fixedly mounted to said wedge guide and to corresponding ones of said tongues for exerting a force onto said wedge yoke.

7. The apparatus in claim 2 wherein said first and second actuators respectively comprise first and second servo-controlled hydraulic cylinders.

8. The apparatus in claim 7 wherein said frame comprises first and second cross heads spaced apart and electrically and mechanically connected together, in a fixed arrangement, by first and second conductive columns, said first and second cross-heads having first and second holes extending therethrough in said first predefined direction and a first insulating bearing lining said first hole; and said apparatus further comprises: a pair of third and fourth cylinders securely connected to said first cross-head and having first and second piston rods; and said force transferring and stopping means further comprises:
a cross bar having two opposing ends and fixedly connected to said first and second pistons in the vicinity of the two opposing ends thereof, for establishing and maintaining, in response to a force exerted thereon by said pair of cylinders, an electrical current path through said specimen, said cross bar further having a coupler for abuttingly engaging with a corresponding coupler attached to an end of a piston of said first cylinder and transferring the mechanical force produced therefrom to said specimen so as to produce the compressive deformation thereof;
an insulating plate fixedly connected at one surface of said plate at substantially a center axial location thereof to said cross bar;
first and second conductive extension shafts, said first extension shaft extending through the first insulating bearing located in said first cross-head so as to be electrically insulated from said first cross head;
a rigid conductor fixedly and electrically connected between a second surface of said insulating plate, opposite to said first surface thereof, and a first end of said first extension shaft;
a substantially U-shaped cross stop having a third hole located axially therethrough and a second bearing lining said third hole for guiding said second shaft along said first and second directions but electrically insulating said second shaft from said cross head;
a stop plate fixedly secured to a first end of said second shaft and situated between a second end of said first shaft and the first end of said second shaft, wherein the stop plate has a diameter greater than that of the third hole and functions to impact against said cross stop during movement of said second shaft in the first direction so as to abruptly halt further movement of said second shaft in said first direction during compressive deformation of said specimen; and
first and second stop bars fixedly securing, through corresponding first and second insulating spacers, said cross stop to the second cross head; and wherein said first and second deforming means respectively comprise first and second electrically conductive anvils and the first anvil is securely mounted to a second surface of said second extension shaft; and wherein said first and second extension shafts, said stop plate and said anvil are in substantial coaxial alignment.

9. The apparatus in claim 8 further comprising a low voltage high current transformer having a secondary winding which is connected between said rigid conductor and said first cross-head so as to provide a controlled source of electrical heating current to said specimen.

10. The apparatus in claim 8 wherein said second deforming means further comprises:
a conductor plate having first and second opposing sides and in electrical communication with said second cross head;
a conductive anvil support having first and second opposing surfaces and mounted at the first surface thereof to the first side of said conductive plate; said second anvil being mounted to the second surface of said anvil support;
a load cell having first and second opposing surfaces, wherein the first surface of the load cell is mounted to the second side of said conductor plate; and
said wedge shaft being securely mounted to the second surface of the load cell; and
wherein said second anvil, the anvil support, the load cell and the wedge shaft are all in substantial coaxial alignment.

11. The apparatus in claim 10 wherein the first and second columns, the first and second conductive shafts, the anvil support and the conductor plate having internal cooling passages.

12. The apparatus in claim 1 wherein the moving means comprises:
a shaft connected at one end to said second deforming means and extending in said first direction therefrom; and wherein
the second actuator is fixedly mounted to said frame and connected to a second end of said shaft.

13. The apparatus in claim 12 wherein said frame comprises first and second cross heads spaced apart and electrically and mechanically connected together, in a fixed arrangement, by first and second conductive columns, said first and second cross-heads having first and second holes extending therethrough in said first predefined direction and a first insulating bearing lining said first hole; and said apparatus further comprises: a pair of third and fourth cylinders securely connected to said first cross-head and having first and second piston rods; and said force transferring and stopping means further comprises:
a cross bar having two opposing ends and fixedly connected to said first and second pistons in the vicinity of the two opposing ends thereof, for establishing and maintaining, in response to a force exerted thereon by said pair of cylinders, an electrical current path through said specimen, said cross bar further having a coupler for abuttingly engaging with a corresponding coupler attached to an end of a piston of said first cylinder and transferring the mechanical force produced therefrom to said specimen so as to produce the compressive deformation thereof;

an insulating plate fixedly connected at one surface of said plate at substantially a center axial location thereof to said cross bar;

first and second conductive extension shafts, said first extension shaft extending through the first insulating bearing located in said first cross-head so as to be electrically insulated from said first cross head;

a rigid conductor fixedly and electrically connected between a second surface of said insulating plate, opposite to said first surface thereof, and a first end of said first extension shaft;

a substantially U-shaped cross stop having a third hole located axially therethrough and a second bearing lining said third hole for guiding said second shaft along said first and second directions but electrically insulating said second shaft from said cross head;

a stop plate fixedly secured to a first end of said second shaft and situated between a second end of said first shaft and the first end of said second shaft, wherein the stop plate has a diameter greater than that of the third hole and functions to impact against said cross stop during movement of said second shaft in the first direction so as to abruptly halt further movement of said second shaft in said first direction during compressive deformation of said specimen; and first and second stop bars fixedly securing, through corresponding first and second insulating spacers, said cross stop to the second cross head; and wherein said first and second deforming means respectively comprise first and second electrically conductive anvils and the first anvil is securely mounted to a second surface of said second extension shaft; and wherein said first and second extension shafts, said stop plate and said anvil are in substantial coaxial alignment.

14. The apparatus in claim 13 further comprising a low voltage high current transformer having a secondary winding which is connected between said rigid conductor and said first cross-head so as to provide a controlled source of electrical heating current to said specimen.

15. The apparatus in claim 13 wherein said second deforming means further comprises:
a conductor plate having first and second opposing sides and in electrical communication with said second cross head;
a conductive anvil support having first and second opposing surfaces and mounted at the first surface thereof to the first side of said conductive plate; said second anvil being mounted to the second surface of said anvil support;
a load cell having first and second opposing surfaces, wherein the first surface of the load cell is mounted to the second side of said conductor plate; and
said wedge shaft being securely mounted to the second surface of the load cell; and
wherein said second anvil, the anvil support, the load cell and the wedge shaft are all in substantial coaxial alignment.

16. The apparatus in claim 15 wherein the first and second columns, the first and second conductive shafts, the anvil support and the conductor plate having internal cooling passages.

17. In a material testing system, apparatus for controllably deforming a specimen comprising:

force producing means, having a first servo-controlled hydraulic cylinder and mounted to a fixed frame, for controllably generating a mechanical force along a first pre-defined direction; said frame having first and second cross heads spaced apart and electrically and mechanically connected together, in a fixed arrangement, by first and second conductive columns, said first and second cross-heads having first and second holes extending therethrough in said first pre-defined direction and a first insulating bearing lining said first hole;

first and second deforming means for compressively deforming a speciment so as to generate a compressive deformation therein, wherein said first and second deforming means comprise first and second electrically conductive anvils which abuttingly engage with corresponding opposing sides of said specimen while the specimen is being deformed;

force transferring and stopping means, situated in abutting engagement with said first deforming means, for moving said first deforming means, in response to said force, along said first pre-defined direction so as to compressively deform said specimen and for terminating further movement of said first deforming means as soon as said first deforming means has compressed said specimen by a predetermined amount; said force transferring and stopping means comprising:

a cross bar having two opposing ends and fixedly connected to said first and second pistons in the vicinity of the two opposing ends thereof, for establishing and maintaining, in response to a force exerted thereon by said pair of cylinders, an electrical current path through said specimen, said cross bar further having a coupler for abuttingly engaging with a corresponding coupler attached to an end of a piston of said first cylinder and transferring the mechanical force produced therefrom to said specimen so as to produce the compressive deformation thereof;

an insulating plate fixedly connected at one surface of said plate at substantially a center axial location thereof to said cross bar;

first and second conductive extension shafts, said first extension shaft extending through the first insulating bearing located in said first cross-head so as to be electrically insulated from said first cross head;

a rigid conductor fixedly and electrically connected between a second surface of said insulating plate, opposite to said first surface thereof, and a first end of said first extension shaft;

a substantially U-shaped cross stop having a third hole located axially therethrough and a second bearing lining said third hole for guiding said second shaft along said first and second directions but electrically insulating said second shaft from said cross head;

a stop plate fixedly secured to a first end of said second shaft and situated between a second end of said first shaft and the first end of said second shaft, wherein the stop plate has a diameter greater than that of the third hole and functions to impact against said cross stop during movement of said second shaft in the first direction so as to abruptly halt further movement of said second shaft in said first direction during compressive deformation of said specimen; and first and second stop bars fixedly securing, through corresponding first and second insulating spacers, said cross stop to the second cross head;

moving means, having a second servo-controlled hydraulic cylinder and coupled to said second deforming means and mounted to the fixed frame, and operative in response to the second hydraulic cylinder, for moving said specimen and said first and second deforming means by the pre-determined amount and in a second direction opposite to the first pre-defined direction prior to commencement of said compressive deformation, wherein said moving means experiences substantially no movement in said first pre-defined direction while said specimen is being compressively deformed; said moving means comprising:

a wedge shaft connected at one end to said second deforming means and extending in said first direction therefrom;

a wedge having a first inclined surface;

a wedge guide fixedly connected to said frame for guiding movement of said wedge along third and fourth directions, said third and fourth directions being opposite to each other and substantially perpendicular to said first and second directions;

a wedge yoke connected to said wedge shaft at a second end thereof and having a second inclined surface complementary to said first inclined surface for slidably engaging with said first inclined surface so as to move said wedge yoke in either said first or second directions as said wedge yoke is moved in said third or fourth directions, wherein said wedge yoke moves at a pre-defined proportion of distance and rate at which said wedge moves while in sliding engagement therewith; and wherein the second hydraulic cylinder is connected to said wedge at one end thereof for controllably moving said wedge through a desired distance in either said third or fourth directions; and wherein the first anvil is securely mounted to a second surface of said second extension shaft; and wherein said first and second extension shafts, said stop plate and said anvil are in substantial coaxial alignment;

whereby strain rate and final strain induced in the specimen during said compressive deformation are respectively and substantially independently determined by velocity of said force transferring and stopping means along said first direction during said deformation and a distance that said moving means is moved in said second pre-defined direction prior to said deformation.

18. The apparatus in claim 17 wherein said wedge guide comprises:

a first groove situated along said third and fourth directions for guiding said wedge for movement therealong; and a second groove intersecting with and substantially perpendicular to said first groove for guiding said wedge yoke along said first and second directions in response to movement of said wedge.

19. The apparatus in claim 18 wherein said wedge guide further comprises a wear plate situated between a rear surface of said wedge and an opposing parallel surface of said wedge guide and fixedly secured to said wedge guide for providing a wearing surface for slidable engagement with the rear surface of the wedge; and wherein the rear surface of the wedge and the wearing surface of the wear plate, and the first and second inclined surfaces are roughened so as to provide increased sliding friction therebetween.

20. The apparatus in claim 18 further comprising a low voltage high current transformer having a secondary winding which is connected between said rigid conductor and said first cross-head so as to provide a controlled source of electrical heating current to said specimen.

21. The apparatus in claim 18 wherein said second deforming means further comprises:

a conductor plate having first and second opposing sides and in electrical communication with said second cross head;

a conductive anvil support having first and second opposing surfaces and mounted at the first surface thereof to the first side of said conductive plate; said second anvil being mounted to the second surface of said anvil support;

a load cell having first and second opposing surfaces, wherein the first surface of the load cell is mounted to the second side of said conductor plate; and said wedge shaft being securely mounted to the second surface of the load cell; and wherein said second anvil, the anvil support, the load cell and the wedge shaft are all in substantial coaxial alignment.

22. The apparatus in claim 21 wherein the first and second columns, the first and second conductive shafts, the anvil support and the conductor plate having internal cooling passages.

23. In a dynamic thermal-mechanical material testing system, a method for simultaneously imparting predefined thermal and deformation profiles to a test specimen, comprising the steps of:

imparting a mechanical deformation to a specimen comprising:

controllably generating, through a first actuator mounted to a fixed frame, a mechanical force along a first pre-defined direction;

compressively deforming the specimen, using first and second deforming means, so as to generate a compressive deformation therein, wherein said first and second deforming means abuttingly engage with corresponding opposing sides of said specimen while the specimen is being deformed;

first moving said first deforming means, in response to said force, along said first pre-defined direction so as to compressively deform said specimen and terminating further movement of said first deforming means as soon as said first deforming means has compressed said specimen by a pre-determined amount; and second moving, using a wedge assembly coupled to both said second deforming means and mounted to the fixed frame and having a second actuator, said specimen and said first and second deforming means by the pre-determined amount and in a second direction opposite to the first predefined direction prior to commencement of said compressive deformation; and imparting a thermal profile to said specimen substantially simultaneously with said mechanical deformation comprising:

establishing an electrical current path through said specimen prior to the commencement of said compressive deformation; and passing a controlled amount of electrical current through said path at least while said compressive deformation is occurring so as to self-resistively heat said specimen in order to generate both a desired heating rate and isothermal planes at a desired corresponding temperature substantially throughout a work zone of the specimen.

24. The method in claim 23 wherein said second moving step comprises the step of moving said second actuator by a pre-defined amount in a third or fourth direction and substantially perpendicular to said first and second directions so as to move said specimen and said first and second deforming means by the pre-determined amount, said pre-defined amount being greater than said pre-determined amount.

25. The method in claim 23 wherein said thermal profile imparting step further comprises the step of conductively cooling the specimen so as to generate a desired cooling rate and a desired corresponding temperature in said specimen work zone.

26. The method in claim 23 further comprising the steps of:

repeating said mechanical deformation imparting step for each deformation in a sequence thereof so as to generate a pre-defined multiple hit deformation profile in said specimen;

generating a desired temperature profile in said specimen concurrently while said pre-defined multiple hit is being produced by either passing a controlled amount of electrical current through said specimen so as to self-resistively heat the specimen at a desired heating rate or conductively cooling the specimen at a desired cooling rate in order to provide isothermal planes at an essentially uniform temperature substantially throughout the work zone of the specimen.

* * * * *

UNITED STATES PATENT AND TRADEMARK OFFICE
CERTIFICATE OF CORRECTION

PATENT NO. : 5,092,179

DATED : March 3, 1992

INVENTOR(S) : Hugo S. Ferguson

It is certified that error appears in the above-identified patent and that said Letters Patent is hereby corrected as shown below:

| | |
|---|---|
| Column 25, Claim 8, line 29: | delete "pistons" and replace by --piston rods-- |
| Column 25, Claim 8, line 37: | after "piston" insert --rod-- |
| Column 25, Claim 8, line 58: | delete "head" and replace by --stop-- |
| Column 26, Claim 13, line 61: | delete "pistons" and replace by --piston rods-- |
| Column 26, Claim 13, line 68 | after "piston" insert --rod-- |
| Column 27, Claim 13, line 21 | delete "head" and replace by --stop-- |
| Column 28, Claim 17, line 34: | delete "said" |
| Column 28, Claim 17, line 34: | delete "pistons" and replace by --piston rods-- |

UNITED STATES PATENT AND TRADEMARK OFFICE
CERTIFICATE OF CORRECTION

PATENT NO. : 5,092,179

DATED : March 3, 1992

INVENTOR(S) : Hugo S. Ferguson

It is certified that error appears in the above-identified patent and that said Letters Patent is hereby corrected as shown below:

Column 28, Claim 17, line 37:   delete "said" and replace by --a--

Column 28, Claim 17, line 37:   after "of" insert --third and fourth--

Column 28, Claim 17, line 62:   delete "head" and replace by --stop--

Signed and Sealed this

Twenty-second Day of June, 1993

Attest:

MICHAEL K. KIRK

Attesting Officer      Acting Commissioner of Patents and Trademarks

UNITED STATES PATENT AND TRADEMARK OFFICE
CERTIFICATE OF CORRECTION

PATENT NO. : 5,092,179
DATED      : March 3, 1992
INVENTOR(S) : Hugo S. Ferguson It is certified that error appears in the above-identified patent and that said Letters Patent is hereby corrected as shown below:

Column 24, Claim 2, line 43:    delete "said wedge yoke" and replace by --said wedge--

Column 27, Claim 15, line 62:   delete "said wedge shaft" and replace by --a wedge shaft--

Signed and Sealed this

Fifth Day of April, 1994

Attest:

BRUCE LEHMAN

*Attesting Officer*     *Commissioner of Patents and Trademarks*